United States Patent
Flohr

(10) Patent No.: US 8,971,996 B2
(45) Date of Patent: Mar. 3, 2015

(54) MEDICAL IMAGING METHOD AND ASSOCIATED DEVICE

(75) Inventor: Thomas Flohr, Uehlfeld (DE)

(73) Assignee: Siemens Aktiengesellschaft, Munich (DE)

( * ) Notice: Subject to any disclaimer, the term of this patent is extended or adjusted under 35 U.S.C. 154(b) by 896 days.

(21) Appl. No.: 12/826,939

(22) Filed: Jun. 30, 2010

(65) Prior Publication Data

US 2011/0004112 A1   Jan. 6, 2011

(30) Foreign Application Priority Data

Jul. 2, 2009   (DE) .......................... 10 2009 031 549

(51) Int. Cl.
*A61B 5/05* (2006.01)
*A61B 6/00* (2006.01)
*A61B 5/0456* (2006.01)
*A61B 5/00* (2006.01)

(52) U.S. Cl.
CPC ............... *A61B 6/504* (2013.01); *A61B 5/0456* (2013.01); *A61B 6/541* (2013.01); *A61B 5/7207* (2013.01)
USPC ............. 600/428; 600/522; 378/62; 382/128; 382/131; 382/132

(58) Field of Classification Search
None
See application file for complete search history.

(56) References Cited

U.S. PATENT DOCUMENTS

2007/0032735 A1   2/2007   Bruder et al.

FOREIGN PATENT DOCUMENTS

DE   102005036963 B3   2/2007

*Primary Examiner* — Unsu Jung
*Assistant Examiner* — Joseph M Santos Rodriguez
(74) *Attorney, Agent, or Firm* — Harness, Dickey & Pierce, P.L.C.

(57) ABSTRACT

A medical imaging method and associated device for generating an image data record of a recording region of a patient, which region is influenced by a cyclical cardiac motion, in which an EKG signal is used to derive a series of recording pulses matched to the cardiac motion, by which pulses the imaging is actuated in a pulsed fashion. In at least one embodiment, a time window of a future recording pulse is calculated taking into account at least one dispersion parameter characterizing the variation in the cycle duration and a location parameter characterizing the expected value of the cycle duration, wherein the dispersion parameter is included into the calculation of the time window using a weighting determined on the basis of the location parameter. Taking into account the dispersion parameter depending on the location parameter allows a reduction in the applied X-ray dose in the situations with irregular heart rates when a low mean heart rate is present at the same time, without significantly reducing the image quality of the generated image data record.

20 Claims, 2 Drawing Sheets

MEDICAL IMAGING METHOD AND ASSOCIATED DEVICE

PRIORITY STATEMENT

The present application hereby claims priority under 35 U.S.C. §119 on German patent application number DE 10 2009 031 549.7 filed Jul. 2, 2009, the entire contents of which are hereby incorporated herein by reference.

FIELD

At least one embodiment of the invention generally relates to a medical imaging method for generating an image data record of a recording region of a patient, which region is influenced by a cyclical cardiac motion. In at least one embodiment, the invention more particularly relates to a so-called rotation angiography method or a so-called cardio-scan within the scope of computed tomography imaging. At least one embodiment of the invention furthermore generally relates to a device for carrying out at least one embodiment of the method.

BACKGROUND

Medical imaging methods for imaging the heart and the blood vessels in the vicinity of the heart in particular generally have the problem that the body region to be recorded is subjected to a continuous cyclical motion as a result of the heart beat. These circumstances are problematic, particularly in the case of X-ray tomographic recording methods in which the image data record to be generated is calculated by back-projection of a multiplicity of projection images recorded from different projection angles. The image data record generally represents a slice- or volume image of the recording region. The back-projection only works without faults if the projection images on which it is based image a body region during identical motion phases of the heart.

This therefore necessitates synchronizing the recording of the projection images with the cardiac motion of the patient in the case of X-ray tomographic recordings of the heart and/or the blood vessels in the vicinity of the heart such that the imaging is performed in each case during the same motion phase, preferably in the rest phase of the cardiac cycle. Here, corresponding "triggering" is brought about on the basis of the EKG (electrocardiogram) signal from the patient. The EKG-supported control of the imaging is also referred to as "EKG gating". Here, the EKG-supported modulation of the tube current is referred to as "EKG pulsing".

Since it is only the projection images recorded during the rest phases of the cardiac motion that are included in the reconstruction of the image data record, X-ray radiation need only be applied to the patient during the time windows required for registering the projection images. In order to reduce the applied X-ray dose, attempts are therefore made to reduce the radiation as far as possible outside of these time windows. Thus, the imaging methods with EKG pulsing therefore estimate the temporally next time window, i.e. the time window following immediately in the future, on the basis of a certain number of preceding cardiac cycles, and a recording pulse corresponding to the time window calculated in advance is generated in order to modulate the tube current during the imaging.

In order to ensure that the image information required for the image reconstruction is also registered in the case of an erroneous estimate of the time window, the X-ray radiation is generally not switched off completely outside of the predicted time windows but reduced to a certain fraction, e.g. 25%. This allows the set of projection images to be completed by using image information from outside of the time window for reconstructing the image data record, although this is generally connected with a significantly reduced image quality of the reconstructed image data record, in particular with increased image noise.

The time window used for generating the recording pulse is usually determined on the basis of the estimated cycle duration of the next cardiac cycle. In the process, the cycle duration is estimated from a predetermined number of preceding cardiac cycles, with the cycle duration corresponding to the time interval between two successive R-waves (or R-spikes). This time interval is also referred to as the "RR-interval".

The mean value or the median value of the RR intervals determined in this fashion is used as subsequent time window for the recording pulse in the case of conventional imaging methods. Irregularities in the cardiac rhythm, i.e. a change in the cardiac frequency on the timescale, lead to an erroneous calculation of the predicted time windows in this method and thus lead to an impairment in the image quality of the image data record that can be obtained.

Therefore, in order to obtain an improved image quality in the reconstructed image data record, even when there is an irregularity present in the cardiac rhythm, DE 10 2005 036 963 B3 proposes to also take into account a dispersion parameter in the calculation of the time window for the recording pulse, which dispersion parameter characterizes the variation in the cycle duration. By way of example, such a dispersion parameter can be the standard deviation of the cycle duration in respect of a trend of the analyzed cardiac cycles. Here, the time window used to generate the recording pulse, that is to say the length of the time interval at full dose, is increased as the variation in the cycle duration increases, as a result of which the motion phase within the cardiac cycle preselected by the user is hit with increased reliability.

Hence, the projection images required for reconstructing the image data record at a preselected motion phase of the heart can also be obtained from the time window range at a high tube current even if there are variations in the cycle duration, and so a reconstruction of the image data record with an improved image quality is possible. However, the improved image quality in the case of an irregular cardiac rhythm is obtained at the expense of an increased X-ray dose compared to the conventional dose modulation methods because of the increase in the time window during which there is an irradiation of the patient at a high tube current.

SUMMARY

In at least one embodiment, a medical imaging method is designed for generating an image data record of a recording region of a patient, which region is influenced by a cyclical cardiac motion, such that, as a function of the present situation in the case of an irregular cardiac rhythm, an X-ray dose applied to the patient is reduced without there being significant deterioration of the obtained image quality of the generated image data record. At least one embodiment the invention is furthermore directed to specifying a device particularly suited to carrying out at least one embodiment of the method.

In respect of at least one embodiment of the method, provision is made for an EKG signal from a patient to be examined to be used to derive a series of recording pulses matched to the cardiac motion of the patient, by which pulses the imaging is actuated in a pulsed fashion. According to at least one embodiment of the method, a time window for the future recording pulse is calculated here taking into account at least one dispersion parameter characterizing the variation in the cycle duration and a location parameter characterizing the expected value of the cycle duration. In the process, a weighting is determined on the basis of the location parameter, using which weighting the dispersion parameter is included in the calculation of the time window.

"Irregularity of the cardiac rhythm" or "variation in the cycle duration" refers to any temporal change in the cardiac frequency or duration of the cardiac cycle on the timescale of a cardiac cycle or a few cardiac cycles. More particularly, the recording pulses in this case are selected such that they are matched in time to the rest phase of the heart within the cardiac cycle.

Here, at least one embodiment of the invention is based on the discovery that the obtained image quality in the reconstructed image data record at low heart rates is significantly more independent of an exact positioning of the time window within the cardiac cycle than at higher heart rates. In the case of a heart rate of, for example, less than beats per minutes, good images can generally be reconstructed within a whole phase range, e.g. between 50% and 70% of the time interval of a cardiac cycle. Moreover, compared to higher heart rates, relatively high dispersion values for the cycle duration are observed at low heart rates. At low heart rates, the calculation of the time window as described in DE 10 2005 036 963 B3 thus leads to a significant increase in the time interval and hence to a higher X-ray dose being applied to the patient compared to situations in which higher heart rates are present, although precise positioning of the time window is not required in the former situation.

It is for this reason that at least one embodiment of the invention proposes to fix the influence of the dispersion parameter on the calculation of the time window as a function of a location parameter, with the location parameter representing the expected value for the cycle duration. Here, the dispersion parameter is acted upon by weighting factors such that the dispersion parameter has little or no effect on the calculation of the time window at low heart rates, and that the influence of the dispersion parameter increases in the calculation as the heart rate increases.

As a result of this, the time window is not or only hardly enlarged at low heart rates, despite high dispersion values being determined. Thus, a possibly occurring erroneous positioning of the time window within the cardiac cycle is deliberately accepted in this situation. This is because erroneous positioning of the time window at low heart rates has no significant influence on the image quality since the cycle duration is comparatively long and hence the time interval of the rest phase of the heart suitable, in principle, for registering projection images is long compared to the required time window for the recording pulse.

In contrast thereto, the dispersion parameter is taken evermore into account as the heart rates increase, and so the time window is increased in these situations if high dispersion or a large standard deviation of the cycle duration is determined so that all projection images required for reconstructing the image data record are obtained with a high probability from the recording pulse. Since the time interval that is suitable in principle for registering projection images is in this situation only insignificantly longer compared to the time window for the recording pulse, a small erroneous positioning of the time window would already result in the risk of insufficient projection images for the rest phase of the heart being present within the recording pulse.

The functional dependence between the location parameter and the weighting of the dispersion parameter is advantageously fixed in advance by empirical means for all EKG-triggered imaging methods. In the simplest case, the dispersion parameter is acted upon by weighting factors between the values of 0 and 1 as a function of the determined mean value of the cycle duration.

The location and length of the time window is fixed by calculating two times. Here, a start time fixes the start of the time window in the direction of increasing time and hence the start of the recording pulse at a high tube current. An end time correspondingly fixes the end of the recording window in the direction of increasing time and hence the end of the recording pulse, where a switch is made from a high tube current to a low tube current.

Thus, the method according to at least one embodiment of the invention can obtain a reduction in the applied X-ray dose at low heart rates compared to the method known from DE 10 2005 036 963 B3, without there being a significant reduction in the image quality of the generated image data record. At the same time, the advantages of taking into account the dispersion parameter at high heart rates remain due to a stronger weighting of the dispersion parameter in the calculation of the time window.

At least one of the dispersion parameters and/or the location parameter is/are preferably determined statistically by analyzing a predetermined number of preceding cardiac cycles.

Herein, the minimum duration, the maximum duration of the analyzed cardiac cycles or the standard deviation of the cycle duration is regarded alone or in combination as dispersion parameter or parameters. A trend in the cycle duration over the analyzed cardiac cycles and possibly the standard deviation from the determined trend is/are additionally or alternatively regarded as dispersion parameter or parameters. Here, a trend refers to a function of the cycle duration determined by a regression (in particular a linear regression), which function characterizes an averaged change in the cycle duration during the analyzed preceding cardiac cycles and allows extrapolative determination of the future cycle duration.

The arithmetic mean value or the median value of the cycle duration of the analyzed cardiac cycles is regarded alone or in combination as the location parameter for characterizing the expected value of the cycle duration. As a result of the nonlinear connection between the input values and the result value in the case of median filtering, individual outliers in the cycle duration of the analyzed cardiac cycles in particular can be suppressed, which outliers are for example caused by extrasystoles and would lead to a mean cycle duration that was erroneously estimated too low.

The imaging method of at least one embodiment is preferably an imaging method based on X-ray radiation, in particular an X-ray tomographic method, in which a multiplicity of X-ray projection images are recorded from varying projection angles, with the image data record being generated from these images by back-projection. The imaging is actuated according to the requirements of the recording pulses under the application of X-ray radiation on the patient such that the X-ray dose applied to the patient is switched to a comparatively high recording value during each recording pulse and to a comparatively low base value between two successive recording pulses, in particular to approximately 25% of the recording value.

A dose modulation is for example obtained on the basis of a modulation of the tube current, which, as a function of the length and position of the time window for the recording pulse, is alternately switched between a high tube current value within the time window, for example 800 mA, and a low tube current value outside of the time window, for example 200 mA.

The EKG pulsing principle according to at least one embodiment of the invention can in principle also be utilized advantageously within the scope of other medical imaging methods in which synchronizing the imaging with the heart beat is necessary or expedient.

According to at least one embodiment of the invention, the device comprises an imaging unit for generating an image data record of a recording region of a patient, which region is influenced by a cyclical cardiac motion, and an EKG unit for registering an EKG signal of the cardiac rhythm of the patient. The device furthermore comprises a control unit that is designed to "trigger" the imaging unit according to at least one embodiment of the method described above, i.e. to actuate the imaging unit in a pulsed fashion matched to the cardiac rhythm of the patient.

In particular, the imaging unit is an X-ray tomography scanner in the broader sense, more particularly a computed tomography scanner or a rotational angiography scanner. The imaging unit correspondingly advantageously comprises an X-ray emitter-detector unit that can rotate about an axis and is used for recording X-ray projection images, and an evaluation unit that is designed to generate the image data record by numerical back-projection from a multiplicity of X-ray projection images recorded at different projection angles.

BRIEF DESCRIPTION OF THE DRAWINGS

In the following text, example embodiments of the invention will be explained in more detail on the basis of schematic drawings, in which.

Mutually corresponding parts and variables are always provided with the same reference signs in all figures.

DETAILED DESCRIPTION OF THE EXAMPLE EMBODIMENTS

Figure 1:
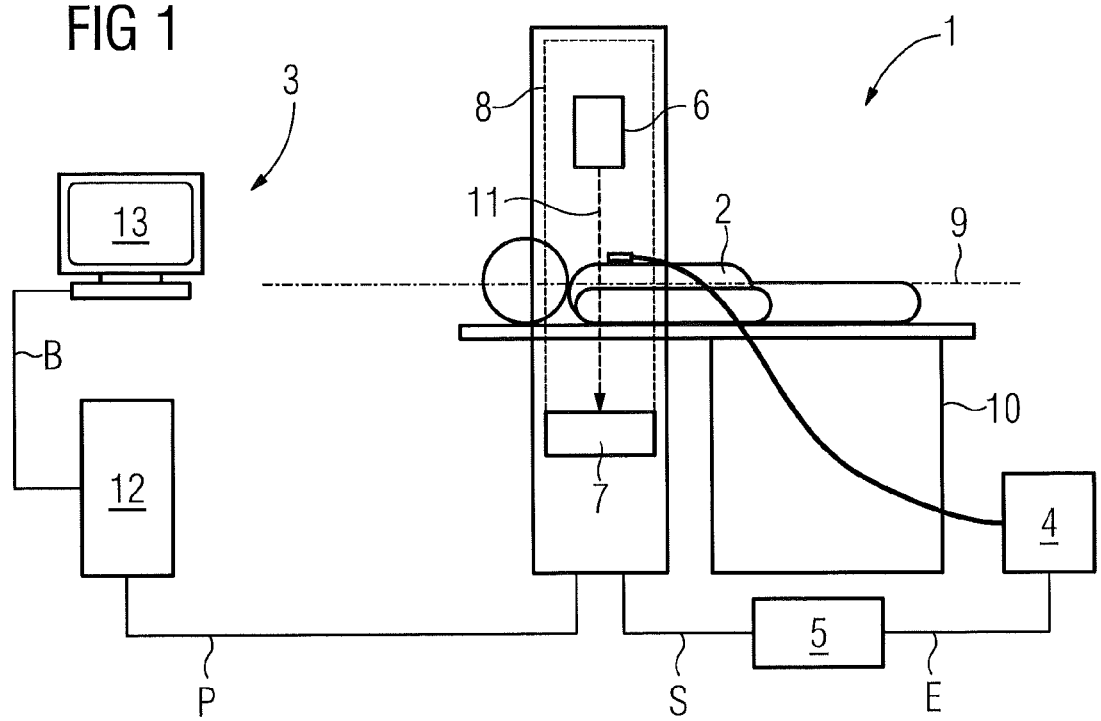
FIG. 1 shows an X-ray tomographic device, in this case a computed tomography scanner suitable for carrying out the method according to an embodiment of the invention.

Various example embodiments will now be described more fully with reference to the accompanying drawings in which only some example embodiments are shown. Specific structural and functional details disclosed herein are merely representative for purposes of describing example embodiments. The present invention, however, may be embodied in many alternate forms and should not be construed as limited to only the example embodiments set forth herein.

Accordingly, while example embodiments of the invention are capable of various modifications and alternative forms, embodiments thereof are shown by way of example in the drawings and will herein be described in detail. It should be understood, however, that there is no intent to limit example embodiments of the present invention to the particular forms disclosed. On the contrary, example embodiments are to cover all modifications, equivalents, and alternatives falling within the scope of the invention. Like numbers refer to like elements throughout the description of the figures.

It will be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of example embodiments of the present invention. As used herein, the term "and/or," includes any and all combinations of one or more of the associated listed items.

It will be understood that when an element is referred to as being "connected," or "coupled," to another element, it can be directly connected or coupled to the other element or intervening elements may be present. In contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

The terminology used herein is for the purpose of describing particular embodiments only and is not intended to be limiting of example embodiments of the invention. As used herein, the singular forms "a," "an," and "the," are intended to include the plural forms as well, unless the context clearly indicates otherwise. As used herein, the terms "and/or" and "at least one of" include any and all combinations of one or more of the associated listed items. It will be further understood that the terms "comprises," "comprising," "includes," and/or "including," when used herein, specify the presence of stated features, integers, steps, operations, elements, and/or components, but do not preclude the presence or addition of one or more other features, integers, steps, operations, elements, components, and/or groups thereof.

It should also be noted that in some alternative implementations, the functions/acts noted may occur out of the order noted in the figures. For example, two figures shown in succession may in fact be executed substantially concurrently or may sometimes be executed in the reverse order, depending upon the functionality/acts involved.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, term such as "below" can encompass both an orientation of above and below. The device may be otherwise oriented (rotated 90 degrees or at other orientations) and the spatially relative descriptors used herein are interpreted accordingly.

Although the terms first, second, etc. may be used herein to describe various elements, components, regions, layers and/or sections, it should be understood that these elements, components, regions, layers and/or sections should not be limited by these terms. These terms are used only to distinguish one element, component, region, layer, or section from another region, layer, or section. Thus, a first element, component, region, layer, or section discussed below could be termed a second element, component, region, layer, or section without departing from the teachings of the present invention.

FIG. 1 shows an X-ray tomographic device 1, in this case a computed tomography scanner, for generating an in particular two- or three-dimensional image data record B in the form of a slice- or volume-image of a recording region influenced by the cardiac motion of a patient 2, in particular in the region of the heart or the blood vessels of the patient 2.

The device 1 substantially comprises an imaging unit 3, an EKG unit 4 and a control unit 5.

The imaging unit 3 comprises an X-ray emitter 6 and an X-ray detector 7, which are attached opposing one another to a rotary frame 8 of a gantry. Here, the rotary frame 8 is mounted in a rotatable fashion such that the X-ray emitter 6 and the X-ray detector 7 are rotated about a common isocentric axis 9 when the rotary frame 8 is rotated.

In order to support the patient 2, the device 1 furthermore comprises a patient couch 10, on which the patient 2 is supported such that a body region to be examined of the patient 2—i.e. in particular the heart or the blood vessels to be examined—is positioned between the X-ray emitter 6 and the X-ray detector 7, and hence more particularly in the beam path 11 of the X-ray radiation emitted by the X-ray emitter 6 in the direction of the X-ray detector 7.

Within the scope of imaging, a multiplicity of X-ray projection images P are recorded from different projection directions by the imaging unit 3 whilst the rotary frame 8 is rotating. The X-ray projection images P are fed to an evaluation unit 12, which calculates the image data record B from the X-ray projection images P, for example by numerical back-projection. In order to display the image data record B, the imaging unit 3 furthermore comprises input and output means, more particularly a monitor 13.

In order to avoid falsification of the image data record B as a result of movement artifacts, which can be traced back to cardiac motion, during the reconstruction of said image data record B from the projection images, the imaging unit 3 is actuated by the control unit 5 such that the projection images P are recorded during certain phases of the cardiac motion corresponding to one another, in particular during the rest phases of the cardiac motion. The control unit 5 determines these phases on the basis of an EKG signal E of the cardiac rhythm of the patient 2, which rhythm is registered by the EKG unit 4 and fed to the control unit 5 as an input variable.

The control unit 5 in turn generates a control signal S that is fed to the imaging unit 3 for actuating the X-ray emitter 6 and the X-ray detector 7.

Figure 2:
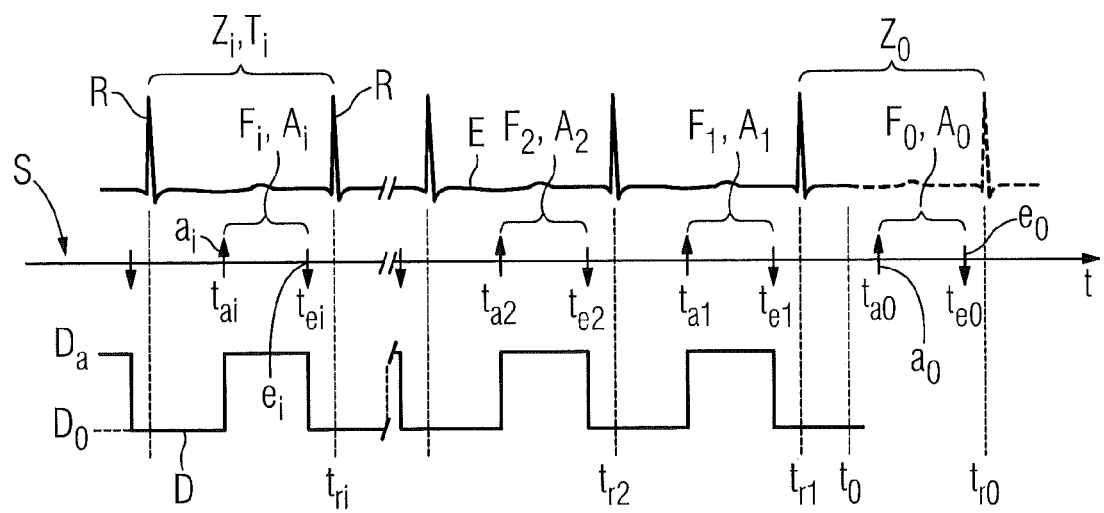
FIG. 2 shows a schematic diagram over time of an EKG signal registered by the EKG unit, a control signal emitted to the imaging unit with a series of recording pulses derived from the EKG signal and the X-ray dose from the imaging unit set according to the requirements of the recording pulses.

As indicated schematically in a diagram over time t in FIG. 2, the control signal S comprises a series of recording pulses $A_i$ (i=0, 1, 2, ... ), each of which is delimited in time by a start signal $a_i$ and an end signal $e_i$ (i=0, 1, 2, ... in each case). The start signal $a_i$ thus marks a start time $t_{ai}$ (i=0, 1, 2, ... ) and the end signal $e_i$ marks an end time $t_{ei}$ (i=0, 1, 2, ... ) of a time window $F_i$ (i=0, 1, 2, ... ) for the respective recording pulse $A_i$. Here, the recording pulses $A_i$ are respectively specified, for example, by one rectangular pulse of the control signal S, wherein the associated start signal $a_i$ is given by a rising edge and the end signal $e_i$ is given by a trailing edge of the control signal S.

In the illustration, already emitted (i.e. past) recording pulses $A_i$ are allocated a positive running index, i.e. i>0, wherein the value of the running index i increases with increasing temporal distance of the recording pulse $A_i$ compared to the current time $t_0$. Compared to the current time $t_0$, the recording pulse following in the immediate future, by contrast, is allocated the running index i=0, i.e. it is referred to as recording pulse $A_0$. Corresponding indexing is used to differentiate the time windows $F_i$, the start and end signals $a_i$, $e_i$, and the associated times $t_{ai}$, $t_{ei}$.

The comparison in FIG. 2 of the control signal S and the EKG signal E shows that the recording pulses $A_i$ are matched to the cardiac rhythm of the patient 2 such that a recording pulse $A_i$ generally takes up a predetermined section of a cardiac cycle $Z_i$ (i=0, 1, 2, ... ), more particularly the time interval spanned between 40% and 70% of the cycle duration $T_i$ (i=0, 1, 2, ... ). Each cardiac cycle $Z_i$ is herein delimited in time by the respective time $t_{ri}$ (i=0, 1, 2, ... ) of two successive R-amplitudes R (or R-spikes) of the EKG signal E.

FIG. 2 likewise shows that the X-ray dose D of the X-ray radiation emitted by the X-ray emitter 6 is in turn controlled according to the requirements of the control signal S, such that the X-ray dose D is set to a comparatively high recording value $D_a$ for the duration of each recording pulse $A_i$, while the X-ray dose D is reduced to a low base value $D_0$, which is approximately 25% of the recording value $D_a$, outside of the recording pulses $A_i$.

In order to output the start signal $a_0$ and the end signal $e_0$ of the future time window $F_0$ of the recording pulse $A_0$, the control unit 5 calculates the associated start and end times $t_{a0}$, $t_{e0}$, wherein the control unit 5 estimates the cardiac cycle duration of the current cardiac cycle $Z_0$ to be expected, which is required for this, by statistically analyzing the last n (n=2, 3, 4, ... ), more particularly n=3, preceding cardiac cycles $Z_1$, $Z_2$, ..., $Z_n$ according to the method described in more detail in DE 10 2005 036 963 B3, the entire contents of which is hereby incorporated herein by reference.

In order to calculate the time window $F_0$, defined by the times $t_{a0}$ and $t_{e0}$, for the recording pulse, the control unit 5 carries out the following calculations:

a) Dispersion Parameter $$\sigma = \frac{\sqrt{\frac{1}{n} \cdot \sum_{i=1}^{n} (T_i + a \cdot i - b)^2}}{\frac{1}{n} \cdot \sum_{i=1}^{n} (a \cdot i - b)} \qquad \text{EQ. 1}$$

The standard deviation 6 of the cycle duration $T_i$ is calculated as the dispersion parameter from the trend-line with the gradient a and axis-intercept b from n preceding cardiac cycles $Z_i$. The gradient a and the axis-intercept b of the trend-line are determined in this case by means of a linear regress.

b) Location Parameter and Weighting Factor $$T_\mu = \frac{1}{n} \cdot \sum_{i=1}^{n} (T_i) \qquad \text{EQ. 2}$$

$$g_0(T_\mu) \in [0, 2.4] \qquad \text{EQ. 3}$$

The mean value $T_\mu$ from n preceding cardiac cycles $Z_i$ is calculated as the location parameter. The mean value $T_\mu$ is subsequently used to determine a weighting factor $g_0$, which is applied to the standard deviation σ when calculating the two times $t_{a0}$ and $t_{e0}$. The weighting factor $g_0$ preferably assumes numbers in a value range between 0 and 2.4 as a function of the mean value $T_\mu$.

Here, the dependence is selected such that in the case of a long mean cycle duration $T_\mu$, i.e. low heart rates, e.g. 55 heart beats per minute, the weighting factor $g_0$ assumes a low value or the value of 0, and so the standard deviation σ has little or no influence on the calculation of the times $t_{a0}$ and $t_{e0}$. Conversely, in the case of a short mean cycle duration $T_\mu$, i.e. high heart rates, e.g. over 80 heart beats per minute, the weighting factor $g_0$ assumes high values of up to 2.4, and so the standard deviation $\sigma$ is very much taken into account in the calculation of the times $t_{a0}$ and $t_{e0}$.

Here, the functional dependence between the mean cycle duration $T_\mu$ and the weighting factor $g_0$ is determined empirically in advance and selected such that a workable compromise is found between the opposing aspects of a maximum reduction in the dose and sufficient reliability in the dimensioning of the time window $F_0$.

c) Maximum $T_{max}$ and Minimum $T_{min}$ Cycle Duration from n Preceding Cardiac Cycles $Z_i$ $$T_{max} = \max\{T_i | i=1,2,\ldots,n\} \qquad \text{EQ. 4}$$

$$T_{min} = \min\{T_i | i=1,2,\ldots,n\} \qquad \text{EQ. 5}$$

d) Data Interval for the Partial Revolution Reconstruction $T_{recon}$ $$T_{recon} = \frac{T_{rot}}{2\pi} \cdot \left(\pi + 2 \cdot \arcsin\left(\frac{R_m}{2R_f}\right) + \alpha_{Trans}\right) \qquad \text{EQ. 6}$$

Here, $T_{rot}$ denotes the time for a complete revolution of the X-ray emitter 6 and the X-ray detector 7 through 360°, $R_m$ (e.g. 250 mm) denotes the typical dimension of a cardiac measurement field, $R_f$ denotes the focal-path radius (e.g. 570 mm) and $\alpha_{Trans} = \pi/12$ denotes the transition of the sinogram weighting used in the reconstruction.

The start and end times $t_{a0}$, $t_{e0}$ of the time window $F_0$, to be calculated in advance, for the recording pulse $A_0$ are now determined according to $$t_{a0} = t_{r1} + p_{Start} \cdot T_{min} \cdot (1 - g_0(T_\mu) \cdot \sigma) \qquad \text{EQ. 7}$$

and $$t_{e0} = t_{r1} - p_{End} \cdot T_{max} \cdot (1 + g_0(T_\mu) \cdot \sigma) + T_{recon} \qquad \text{EQ. 8}$$

wherein $p_{Start}$ and $p_{End}$ define the initial time window for registering the rest phase of the cardiac motion within the cardiac cycle $Z_0$ (e.g. $p_{Start} = 0.4$ and $p_{End} = 0.7$).

The start and end times $t_{pa}$ and $t_{pe}$ of the initial time window correspondingly emerge from:

$$t_{pa} = t_{r1} + p_{Start} \cdot T_{min} \qquad \text{EQ. 9}$$

and $$t_{pe} = t_{r1} + p_{End} \cdot T_{max} + T_{recon} \qquad \text{EQ. 10}$$

Figure 3:
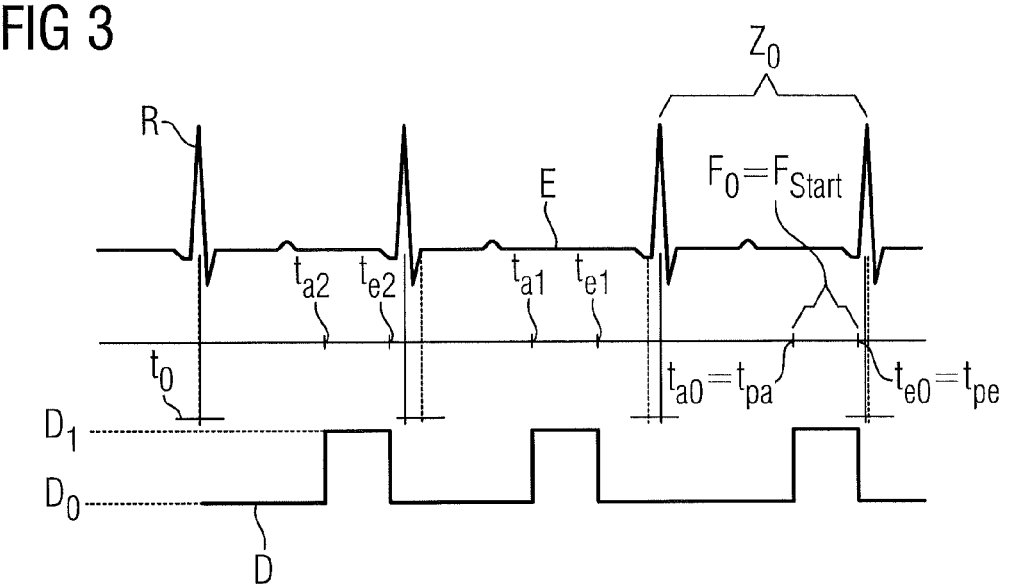
FIGS. 3 and 4 show, in illustrations as per FIG. 2, the EKG signal, the control signal and the X-ray dose at a low and high heart rate.
Figure 4:
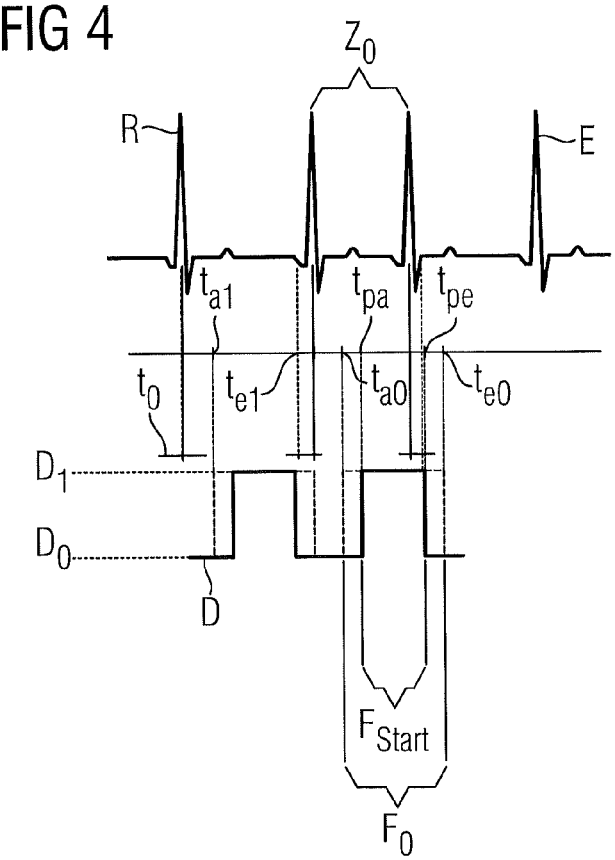

The result of the influence of the standard deviation $\sigma$, controlled by the weighting factor $g_0$, as a function of the mean cycle duration is that the time window $F_0$ fixed by the times $t_{a0}$, $t_{e0}$ remains unchanged compared to the initial time window at low heart rates and increases at high heart rates. These circumstances are shown in the two FIGS. 3 and 4, wherein FIG. 3 shows the situation for low heart rates and FIG. 4 shows the situation for higher heart rates. Here, the R-spikes R occur around an expected value within a dispersion interval $t_\sigma$ fixed by the standard deviation $\sigma$. In the situation shown in FIG. 3 for low heart rates, the rest phase is hit well enough even without taking into account the standard deviation $\sigma$, and so there is no need for enlarging the time window $F_0$ compared to the initial window $F_{start}$. In contrast thereto, the situation shown in FIG. 4 for high heart rates may lead to part of the initial time window $F_{start}$ already also comprising the R-wave. By taking into account the standard deviation $\sigma$ with the weighting $g_0$, the time window $F_0$ is enlarged compared to the initial time window such that there are enough projections available in respect of the rest phase of the cardiac motion during the recording pulse $A_0$ in order to generate the data record.

Due to various latencies in the system components (signal transmission, recognition of the R-amplitudes, etc.) the information relating to the occurrence of an R-amplitude R is delayed by a predetermined period of time. The times used for the calculation should in this case always be understood as specifications in the true time, i.e. corrected for the latencies, provided that the calculated events occur later than at the current time.

At least one embodiment of the invention relates to a medical imaging method and associated device for generating an image data record of a recording region of a patient 2, which region is influenced by a cyclical cardiac motion, in which an EKG signal E is used to derive a series of recording pulses $A_i$, $A^*$ matched to the cardiac motion, by which pulses the imaging is actuated in a pulsed fashion, wherein a time window $F_0$ of a future recording pulse $A_0$ is calculated taking into account at least one dispersion parameter $T_{max}$, $T_{min}$, a, b, $\sigma$ characterizing the variation in the cycle duration $T_i$ and a location parameter $T_\mu$ characterizing the expected value of the cycle duration $T_i$, wherein the dispersion parameter $T_{max}$, $T_{min}$ a, b, $\sigma$ is included into the calculation of the time window $F_0$ using a weighting determined on the basis of the location parameter $T_\mu$. Taking into account the dispersion parameter $T_{max}$, $T_{min}$, a, b, $\sigma$ depending on the location parameter $T_\mu$ allows a reduction in the applied X-ray dose in the situations with irregular heart rates when a low mean heart rate is present at the same time, without significantly reducing the image quality of the generated image data record.

The patent claims filed with the application are formulation proposals without prejudice for obtaining more extensive patent protection. The applicant reserves the right to claim even further combinations of features previously disclosed only in the description and/or drawings.

The example embodiment or each example embodiment should not be understood as a restriction of the invention. Rather, numerous variations and modifications are possible in the context of the present disclosure, in particular those variants and combinations which can be inferred by the person skilled in the art with regard to achieving the object for example by combination or modification of individual features or elements or method steps that are described in connection with the general or specific part of the description and are contained in the claims and/or the drawings, and, by way of combinable features, lead to a new subject matter or to new method steps or sequences of method steps, including insofar as they concern production, testing and operating methods.

References back that are used in dependent claims indicate the further embodiment of the subject matter of the main claim by way of the features of the respective dependent claim; they should not be understood as dispensing with obtaining independent protection of the subject matter for the combinations of features in the referred-back dependent claims. Furthermore, with regard to interpreting the claims, where a feature is concretized in more specific detail in a subordinate claim, it should be assumed that such a restriction is not present in the respective preceding claims.

Since the subject matter of the dependent claims in relation to the prior art on the priority date may form separate and independent inventions, the applicant reserves the right to make them the subject matter of independent claims or divisional declarations. They may furthermore also contain independent inventions which have a configuration that is independent of the subject matters of the preceding dependent claims.

Further, elements and/or features of different example embodiments may be combined with each other and/or substituted for each other within the scope of this disclosure and appended claims.

Still further, any one of the above-described and other example features of the present invention may be embodied in the form of an apparatus, method, system, computer program, computer readable medium and computer program product. For example, of the aforementioned methods may be embodied in the form of a system or device, including, but not limited to, any of the structure for performing the methodology illustrated in the drawings.

Even further, any of the aforementioned methods may be embodied in the form of a program. The program may be stored on a computer readable medium and is adapted to perform any one of the aforementioned methods when run on a computer device (a device including a processor). Thus, the storage medium or computer readable medium, is adapted to store information and is adapted to interact with a data processing facility or computer device to execute the program of any of the above mentioned embodiments and/or to perform the method of any of the above mentioned embodiments.

The computer readable medium or storage medium may be a built-in medium installed inside a computer device main body or a removable medium arranged so that it can be separated from the computer device main body. Examples of the built-in medium include, but are not limited to, rewriteable non-volatile memories, such as ROMs and flash memories, and hard disks. Examples of the removable medium include, but are not limited to, optical storage media such as CD-ROMs and DVDs; magneto-optical storage media, such as MOs; magnetism storage media, including but not limited to floppy disks (trademark), cassette tapes, and removable hard disks; media with a built-in rewriteable non-volatile memory, including but not limited to memory cards; and media with a built-in ROM, including but not limited to ROM cassettes; etc. Furthermore, various information regarding stored images, for example, property information, may be stored in any other form, or it may be provided in other ways.

Example embodiments being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. An imaging method comprising:
    receiving an image data record of a recording region of a patient, the region being influenced by a cyclical cardiac motion which cycles at a cycle duration;
    registering an EKG signal of the cardiac motion of the patient;
    determining a dispersion parameter, the dispersion parameter indicating a variation in the cycle duration,
    determining a weight given to the dispersion parameter based on an expected value of the cycle duration,
    deriving a series of recording pulses from the EKG signal, matched to the cardiac motion by calculating a time window of a future recording pulse such that a size of the time window is based on at least (i) the dispersion parameter, (ii) the determined weight given thereto, and (iii) a cardiac frequency of the cyclical cardiac motion, and
    actuating a CT scanner in a pulsed fashion according to the requirements of the derived recording pulses to generate an image.

2. The imaging method as claimed in claim 1, wherein at least one of the dispersion parameter and the variation in the cycle duration is determined statistically by analyzing a number of preceding cardiac cycles.

3. The imaging method as claimed in claim 2, wherein the variation in the cycle duration is a mean value or a median value of the cycle duration of the analyzed cardiac cycles.

4. The imaging method as claimed in claim 3, wherein at least one of a minimum duration and a maximum duration of the analyzed cardiac cycles is regarded as the at least one dispersion parameter.

5. The imaging method as claimed in claim 4, wherein a start time of the time window is determined taking into account the minimum duration and an end time of the time window is determined taking into account the maximum duration of the analyzed cardiac cycles.

6. The imaging method as claimed in claim 3, wherein a standard deviation of the cycle duration of the analyzed cardiac cycles is regarded as the at least one dispersion parameter.

7. The imaging method as claimed in claim 3, wherein a standard deviation of the cycle duration compared to a trend of the cycle duration of the analyzed cardiac cycles is regarded as the at least one dispersion parameter.

8. The imaging method as claimed in claim 2, wherein at least one of a minimum duration and a maximum duration of the analyzed cardiac cycles is regarded as the at least one dispersion parameter.

9. The imaging method as claimed in claim 8, wherein a start time of the time window is determined taking into account the minimum duration and an end time of the time window is determined taking into account the maximum duration of the analyzed cardiac cycles.

10. The imaging method as claimed in claim 2, wherein a standard deviation of the cycle duration of the analyzed cardiac cycles is regarded as the at least one dispersion parameter.

11. The imaging method as claimed in claim 2, wherein a standard deviation of the cycle duration compared to a trend of the cycle duration of the analyzed cardiac cycles is regarded as the at least one dispersion parameter.

12. The imaging method as claimed in claim 1, wherein the imaging is performed under the application of X-ray radiation on the patient, wherein the X-ray dose applied to the patient is switched to a comparatively high recording value during each recording pulse and to a comparatively low base value between two successive recording pulses.

13. The imaging method as claimed in claim 12, wherein the base value corresponds to 25% of the recording value.

14. The imaging method as claimed in claim 1, wherein the image data is recorded by X-ray tomography as a result of recording a multiplicity of X-ray projection images from varying projection angles, the image data record being generated from the multiplicity of X-ray projection images by back-projection.

15. The imaging method as claimed in claim 1, wherein a series of recording pulses from the EKG signal, are matched to the cardiac motion by the calculating.

16. The method of claim 1, wherein an EKG unit is used for the registering of the EKG signal, and a computer device is used for the deriving and the actuating.

17. The method of claim 1, wherein the deriving the series of recording pulses by calculating the time window includes calculating the time window such that as the rate of cardiac motion decreases a weight given to the dispersion parameter in the calculation of the time window decreases.

18. A computed tomographic (CT) device comprising:
a CT scanner configured to generate an image data record of a recording region of a patient, the region being influenced by a cyclical cardiac motion which cycles at a cycle duration;
an electrocardiograph (EKG) configured to register an EKG signal of the cardiac motion of the patient; and
a computer processor configured to,
    determine a dispersion parameter, the dispersion parameter indicating a variation in the cycle duration,
    determine a weight given to the dispersion parameter based on an expected value of the cycle duration,
    derive a series of recording pulses from the EKG signal, matched to the cardiac motion by calculating a time window of a future recording pulse such that a size of the time window is based on at least (i) the dispersion parameter, (ii) the determined weight given thereto, and (iii) a cardiac frequency of the cyclical cardiac motion, and
    actuate the CT scanner in a pulsed fashion according to the requirements of the derived recording pulses to generate an image.

19. The CT device as claimed in claim 18, wherein the CT scanner comprises:
an X-ray emitter-detector unit that is rotatable about an axis and is used for recording X-ray projection images, and
the computer processor configured to generate the image data record by numerical back-projection from a multiplicity of X-ray projection images recorded at different projection angles.

20. The device of claim 18, wherein the controller is configured to calculate the time window such that as the rate of cardiac motion decreases a weight given to the dispersion parameter in the calculation of the time window decreases.

* * * * *